United States Patent [19]

Mayer et al.

[11] Patent Number: 5,042,505
[45] Date of Patent: Aug. 27, 1991

[54] ELECTRONIC ANGULAR POSITION AND RANGE OF MOTION MEASURING DEVICE AND METHOD

[76] Inventors: Tom G. Mayer, 4304 McFarlin, Dallas, Tex. 75205; George V. Kondraske, 1512 W. Lavender La., Arlington, Tex. 76013

[21] Appl. No.: 492,309

[22] Filed: Mar. 7, 1990

Related U.S. Application Data

[63] Continuation of Ser. No. 373,653, Jun. 27, 1989, abandoned, which is a continuation of Ser. No. 5,671, Jan. 21, 1987, abandoned.

[51] Int. Cl.$^5$ .............................. A61B 5/103
[52] U.S. Cl. ................................. 128/781; 128/782
[58] Field of Search ........................ 128/782, 774, 781

[56] References Cited

U.S. PATENT DOCUMENTS

| | | |
|---|---|---|
| 1,083,639 | 1/1914 | Stewart . |
| 2,565,381 | 6/1951 | Leighton . |
| 3,322,115 | 7/1967 | Richards . |
| 3,336,679 | 4/1967 | Davis . |
| 3,791,042 | 10/1971 | Bell . |
| 3,840,726 | 10/1973 | Harrison . |
| 3,908,279 | 9/1973 | Yoslow et al. . |
| 3,962,693 | 8/1976 | Schamblin . |
| 3,991,745 | 8/1976 | Yoslow et al. . |
| 4,037,480 | 5/1977 | Wagner . |
| 4,077,132 | 5/1978 | Erickson . |
| 4,094,073 | 2/1978 | Parra . |
| 4,108,164 | 4/1978 | Hall . |
| 4,157,619 | 10/1979 | Zuvela . |
| 4,167,818 | 9/1979 | Cantarella et al. . |
| 4,172,327 | 9/1979 | Kuehn et al. . |
| 4,196,524 | 5/1980 | Bechtel . |
| 4,219,940 | 11/1980 | Okubo . |
| 4,224,573 | 12/1980 | Brook . |
| 4,279,260 | 7/1981 | Stump . |
| 4,375,727 | 3/1983 | McAdams, Jr. et al. . |
| 4,436,099 | 7/1984 | Raftopoulos . |
| 4,444,204 | 6/1984 | Bryant et al. . |
| 4,485,825 | 6/1984 | Domjan et al. . |
| 4,586,150 | 4/1986 | Budziak et al. . |
| 4,665,978 | 3/1987 | Linial et al. .................. 128/782 |

OTHER PUBLICATIONS

Bunnell, "An Objective Criterion for Scoliosis Screening", vol. 66-A, No. 9, *Spine*, pp. 1381-1387, (Dec. 1984).

Mayer et al., "Use of Noninvasive Techniques for Quantification of Spinal Range-of-Motion in Normal Subjects and Chronic Low-Back Dysfunction Patients", vol. 9, No. 6, *Spine*, pp. 588-595, (1984).

*Primary Examiner*—Max Hindenburg
*Assistant Examiner*—John C. Hanley

[57] ABSTRACT

An electronic device for measuring relative angular positional displacement and angular range of motion for body segments and articulating joints of the human skeleton is disclosed. The device has a hand-held interface unit which is placed against the body segment or joint to be tested. Mounted within the housing of the interface unit is a shaft with a pendulum at one end and an optical encoder at the other. As the body segment rotates or the joint articulates, the pendulum swings in the direction of gravity, causing the shaft to rotate. The optical encoder generates an electrical signal representative of the amount of rotation of the shaft. The generated signal is fed to a microprocessor which processes the information and can produce on a display the change in angular position relative to initial angular position or the angular range of motion of the body segment or articulating joint.

5 Claims, 9 Drawing Sheets

ELECTRONIC ANGULAR POSITION AND RANGE OF MOTION MEASURING DEVICE AND METHOD

This is a continuation of application Ser. No. 373,653, filed on June 27, 1989, now abandoned, which in turn was a continuation of Ser. No. 005,671, filed Jan. 21, 1987, and abandoned.

FIELD OF THE INVENTION

This invention relates to an electronic device and method for accurately and quickly measuring the relative angular positional displacement and the angular range of motion for body segments and articulating joints of the human skeleton.

BACKGROUND OF THE INVENTION

Measuring relative angular positional displacement and the angular range of motion for body segments and articulating joints of the human skeleton is of value in the medical and rehabilitation fields. For example, with reference to the human spine, the primary spinal range-of-motion measurements, postural zero (straight up) to full flexion, postural zero to hyper-extension, postural zero to full left lateral bend, and postural zero to full right lateral bend, are used as part of the diagnosis of various spine and back-muscle disorders and diseases. As a patient engages in physical therapy or receives other treatment, the angular range of motion should increase, resulting in a changed measured value. However, prior instruments for measuring relative angular position and angular range of motion have not been found to be effective or accurate.

In the past, doctors, clinicians and other medical professionals and paraprofessionals have measured the relative angular position and the angular range of motion for body segments and articulating joints of the human skeleton using mechanical inclinometers. These prior instruments were designed for use by plumbers and carpenters and therefore lack necessary features for use on the human skeleton. Such instruments are accurate only within plus or minus 1° over a 360° range, an accuracy which is not sufficient, for example, for the measurements made of the angular range of motion of the human spine, where an accuracy within plus or minus 0.5° is desired. Mechanical inclinometers are often large and bulky and cannot be easily stabilized against the body segment or articulating joint, making it impossible to duplicate test conditions for two different measurements. Also, such instruments, because they do not have computational ability built into them, lack the ability to compute differential angles between two body segments. Further, such instruments are unsuitable for measurements in the lateral plane, as when a person bends from side to side at the waist.

There has been a need for an easy to use, hand-held device which avoids the above-described problems.

SUMMARY OF THE INVENTION

This invention is directed to a hand-held electronic device for measuring relative angular positional displacement for body segments and articulating joints of the human skeleton.

The device comprises a hand-held interface unit adapted for placement against the body segment or articulating joint. Generating means in the unit generates an electrical signal representative of a second angular position relative to a first angular position.

In one embodiment, the generating means comprises an optical encoder mounted on a first end of a shaft and a pendulum mounted on a second end of the shaft, whereby the pendulum swings in the direction of the force of gravity as the body segment moves or the joint articulates, thereby causing the shaft to rotate, the encoder measuring the rotational motion of the shaft. The optical encoder generates an electrical signal in the form of electrical pulses representative of the rotational motion of the shaft.

A microprocessor, electrically connected to the interface unit, processess the generated electrical signal and provides a measurement of the second angular position relative to the first angular position, or a measurement of angular range of motion.

This invention is also directed to a related method for measuring relative angular positional displacement.

DETAILED DESCRIPTION OF THE INVENTION

Figure 1:
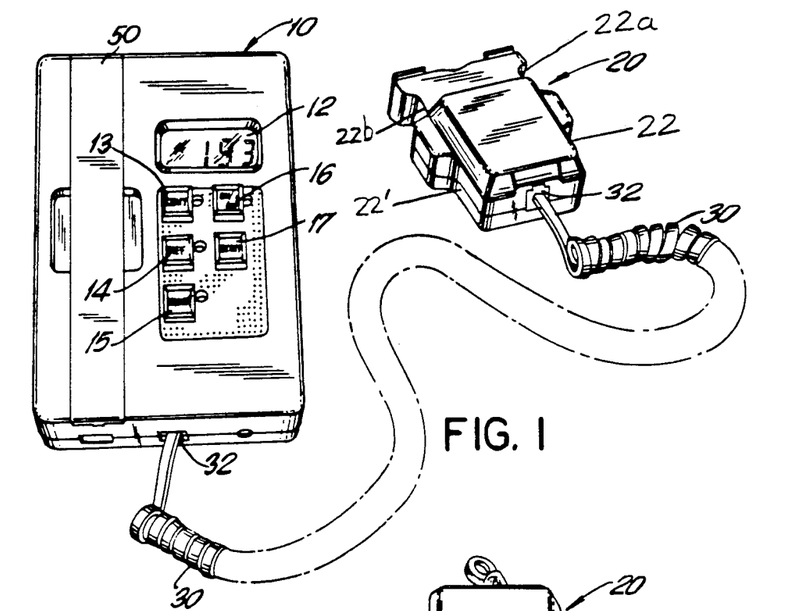
FIG. 1 is a perspective view of a hand-held interface unit and a control unit for the device of the present invention.

The device of the present invention allows for accurate and fast measurement of relative angular positional displacement and angular range of motion for body segments and articulating joints of the human skeleton. The preferred embodiment of the device of the present invention includes a control unit 10 and a hand-held interface unit 20, connected to one another by a flexible electrical cord 30, as shown in FIG. 1. As described below, there are also two attachments, one a lateral plane attachment 40 for measurement of relative angular positional displacement and angular range of motion in a lateral plane (the side-to-side movement shown in FIG. 10), and the other an x-ray attachment 50 for measurement of angular differences on an x-ray film.

The preferred embodiment of the device of the present invention is intended to measure relative angular positional displacement and angular range of motion for the following motions of the human skeleton: postural zero (straight up) to full flexion; postural zero to hyperextension; postural zero to full left lateral bend; and postural zero to full right lateral bend. The invention may be used, however, to measure any relative angular positional displacement and any angular range of motion of the human skeleton.

The control unit 10, shown in FIGS. 1, 2, 3 and 4, is made, for example, from injection molded polycarbonate, which is chemically stable against any and all cleaning solutions used in hospital and clinical environments. The control unit 10 contains a conventional microprocessor (not shown), for example, an NEC 78C10. Also within the control unit 10 is a display 12, for example a liquid crystal display, and a power source (not shown), for example, six size AA rechargeable batteries. In the embodiment shown in FIGS. 1 and 2, five membrane switches 13-17 are located below the display 12. Switch 16 turns the control unit 10 on and off. Switches 13-15 are so-called protocol switches, and set the mode in which the device will operate. The description of exemplary protocols is set forth below in the section entitled "Protocol Selection". The final switch is labeled "Reset" and is used to reset the control unit 10 for a new measurement.

Figure 3:
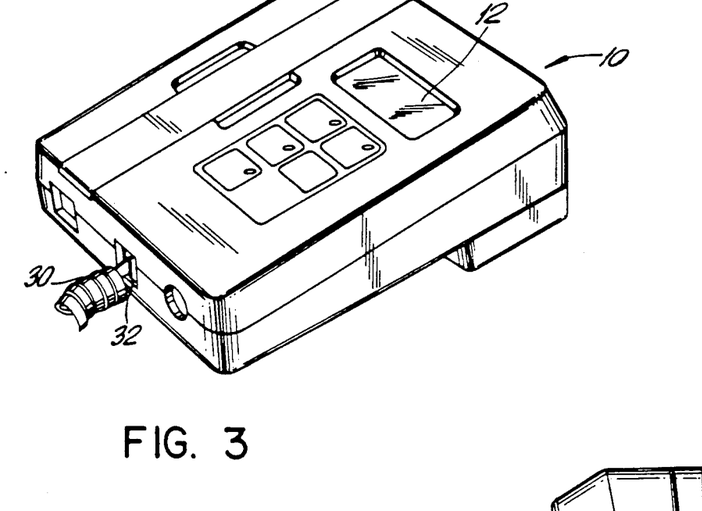
FIG. 3 is a perspective view of the control unit showing the control unit on a flat surface at approximately a 10° tilt.
Figures 4, 5:
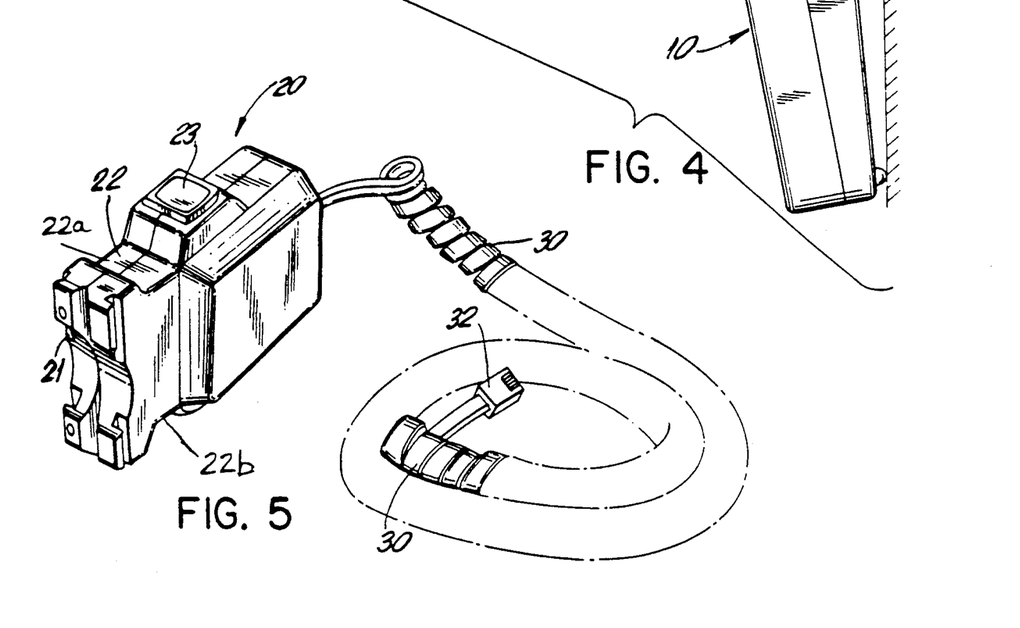
FIG. 4 is a side elevational view showing the control unit mounted on a bracket on a wall.
FIG. 5 is a perspective view of the interface unit alone, showing the profile of a front end of the interface unit and the location of a set button on a top end of the interface unit.
Figure 6:
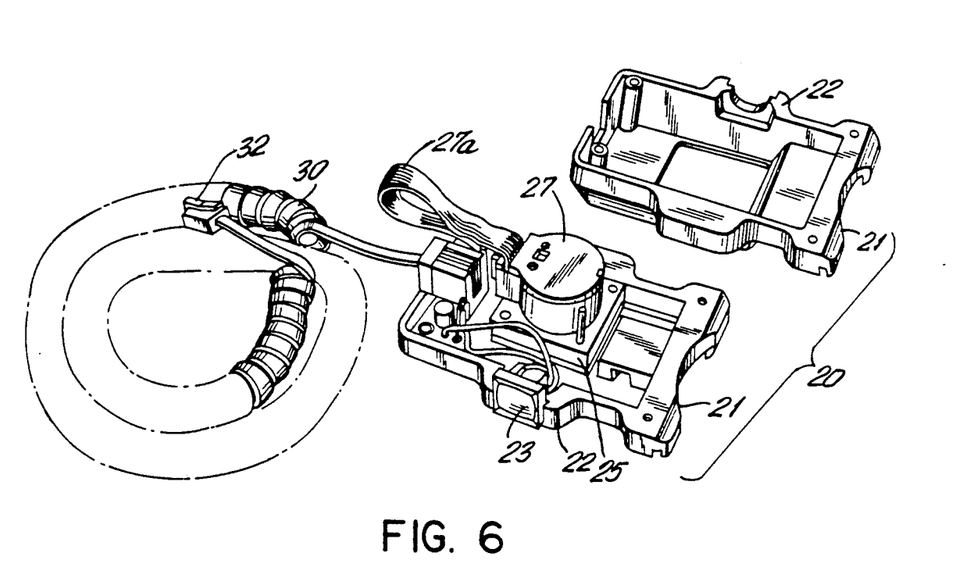
FIG. 6 is a perspective view of the interface unit showing some of the internal components, including an optical encoder.
Figure 7:
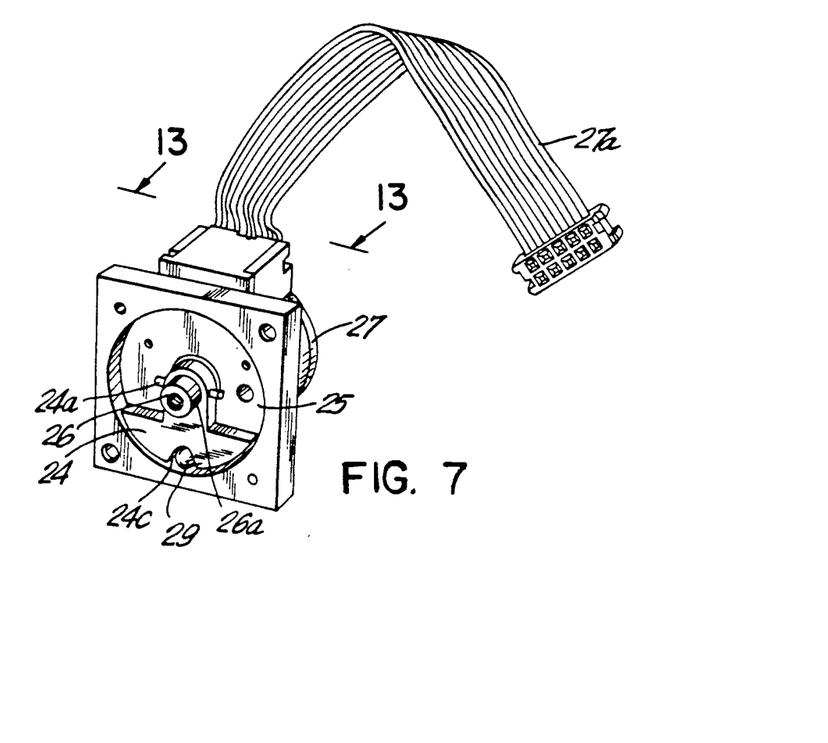
FIG. 7 is a perspective view of a portion of the interface unit showing some of the internal components, including a pendulum, a precision ball located in a groove of the pendulum, a pendulum housing and a shaft within the housing.

For ease of use, the control unit 10 has a bracket (not shown) so that the control unit 10 can be mounted on a wall perpendicular to the line of sight, for easy reading of the display 12, as shown in FIG. 4. The control unit 10 may also be tilted, as shown in FIG. 3, for example 10°, for use on a flat surface such as a desk, to facilitate reading.

Figure 2:
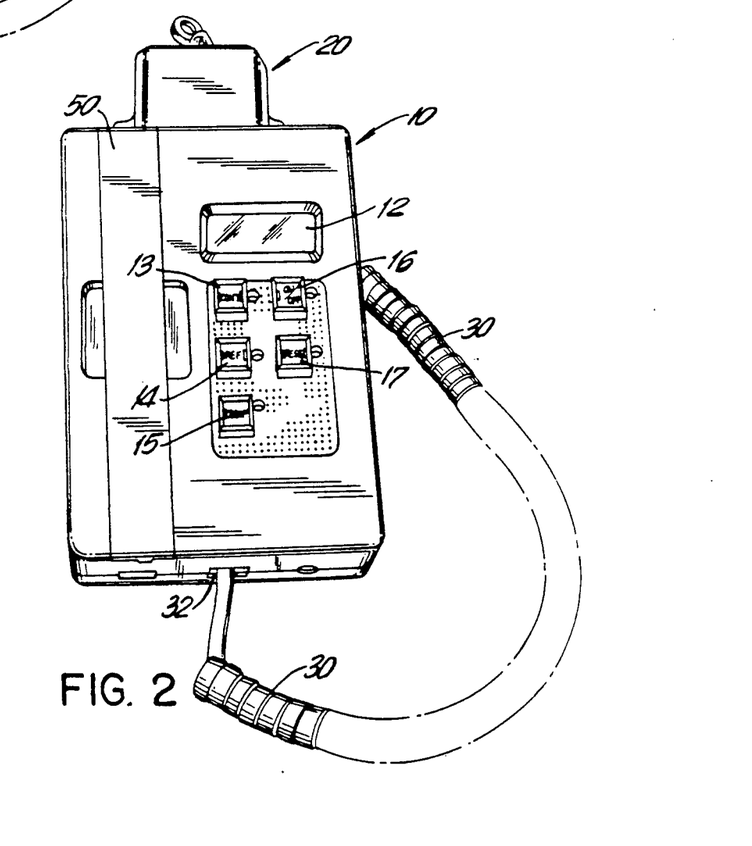
FIG. 2 is a perspective view of the control unit of FIG. 1 with the interface unit stored in a back recess of the control unit.

As seen in FIG. 2, the hand-held interface unit 20 is stored in a back recess of the control unit 10 when not in use.

The flexible electrical cord 30 is used as a path for the transmission of electrical signals in the form of electrical pulses from the hand-held interface unit 20 to the control unit 10. The cord 30 is connected to the control unit 10 and the interface unit 20 by conventional jacks 32.

The hand-held interface unit 20 is shown in detail in FIGS. 5-7 and 13-15. The interface unit 20, for example, is a two-piece, injection molded polycarbonate plastic. The interface unit 20 in the present embodiment is adapted for use on the spine and is 3⅞" long by 5" high and 1 5/16" at its widest point. The profile of the interface unit 20, best seen in FIG. 3, is designed to optimize stabilization against the four regions of the spine; cervical, thoracic, lumbar and sacrum. A front end 21 of the interface unit 20 which makes contact with the body segment or articulating joint is ⅜" wide to facilitate stabilization against the body segment or joint. A flat surface 22a on the top end 22 of the interface unit 20 and a flat surface 22b on a bottom end 22' of the interface unit 20 allow the operator to hold the interface unit 20 in his or her hand when placing the front end 21 of the unit 20 against the body segment or articulating joint. A set button 23 is placed on a top end 22 of the interface unit 20 for use by either right-handed or left-handed persons. The set button 23 is activated in most cases in order to take reference points, in the manner described below in the section entitled "Protocol Selection". The interface unit 20 is also designed to fit comfortably in the hand of the physician or clinician.

Included within the interface unit 20 are a pendulum 24, a pendulum housing 25, a shaft 26 and an optical encoder 27. The shaft 26 runs through a central bore in the housing 25. Ball bearing 28, shown in FIG. 14, which is fixed on its outside to the housing 25 and is fixed on its inside to the shaft 26, permits the shaft 26 to rotate within the housing 25. Retaining ring 28a keeps the bearing 28 on the shaft 26 in a conventional manner.

The pendulum 24 is secured to a first end 26a of the shaft 26 by spring pin 24a. Spring pin 24a passes through pendulum bore 24b, shown in FIG. 15. Any swinging motion of the pendulum 24 will therefore cause the shaft 26 to rotate.

Attached to a second end 26b of the shaft 26 is the optical encoder 27, which, for example, is a Hewlett Packard model HEDS 5300 or any other Hewlett Packard optical encoder in the model HEDS 5000 series. The encoder 27 operates in a conventional manner to translate the amount of rotation of the shaft 26, up to 360°, into a digital electrical signal, in the form of electrical pulses, indicative of the degrees of rotation of the shaft 26.

As previously described, the shaft 26 rotates in response to the movement of the pendulum 24. The pendulum 24 will swing in the direction of the force of gravity as the interface unit 20 changes its angular position in response to the angular movement of the body segment or articulating joint being tested, for example as the patient moves from a postural zero (straight up) position to a flexion position shown in FIG. 8, or to a hyper-extension position shown in FIG. 9. Therefore, the digital electrical signal generated by the encoder 27 is representative of the degrees of angular motion of the body segment or articulating joint being tested.

The electrical signal from the encoder 27, which is in the form of electrical pulses, is transmitted along cable 27a and then along cord 30 to the microprocessor in the control unit 10, which acts as a processing means to process the electrical signal from the encoder 27 in a manner determined by the programming of the microprocessor.

An improvement to the present invention is a device which includes the use of damping means, for example precision ball 29 made of stainless steel located in a groove 24c of the pendulum 24, to dampen the oscillations of the pendulum 24 as the pendulum 21 swings. This prevents inaccurate readings of angular position due to rotation of shaft 26 in response to the oscillations of pendulum 24.

The pendulum 24 has a natural frequency of oscillation at which it will swing as the shaft 26 turns. This frequency is dependent on the distance from the center of the mass of the pendulum 24 to the center of rotation of the shaft 26. The ball 29 also has a natural frequency of oscillation which is dependent on the diameter of the ball 29 and the diameter of the counterbore in the housing 25. The natural frequency of oscillation of the pendulum 24 is different from the natural frequency of oscillation of the ball 29. As the pendulum 24 swings in response to movement of the shaft, the differing natural frequencies of oscillation of the pendulum 24 and the ball 29 cause interference of relative motion between the ball 29 and the pendulum 24, resulting in a resistance between the pendulum 24 and the ball 29 and a damping of the pendulum's oscillations. In a preferred embodiment of the improved device, for improved damping, there is a second identical precision ball directly behind the ball 29 in the groove 24c.

Rapid motion of the device can also cause extreme unwanted acceleration of the pendulum. To prevent such extreme acceleration, the groove 24c has tapered walls. During rapid motion, the ball 29 gets driven between the tapered walls of the groove 24c and the counterbore of the housing 25. This causes a wedging effect which quickly reduces the oscillations of the pendulum 24.

This improvement which includes the damping means is not our invention but rather is the invention of Arthur Sammartano and is the subject of a patent application filed on even date herewith entitled "Improved Electronic Angular Position and Angular Range of Motion Measuring Device with Damping Means". The present application contains a description of the improvement invented by Mr. Sammartano solely to avoid any question regarding the best mode, pursuant to 35 U.S.C. Sec. 112, contemplated by us for carrying out our invention. The inclusion of a description of the improvement in this application should not be construed as an assertion by us that we invented the improvement claimed in Mr. Sammartano's application.

The optical encoder 27 operates in a conventional manner to translate the rotation of the shaft 26 into interruptions of a light beam which are then output as electrical pulses along cable 27a and then along cord 30 to the microprocessor in the control unit 10. A code wheel 27c in the encoder 27, shown in FIG. 14, has, for example, 720 equally spaced apertures around its circumference, permitting measurement of angular rotation within 0.5°.

Figure 14:
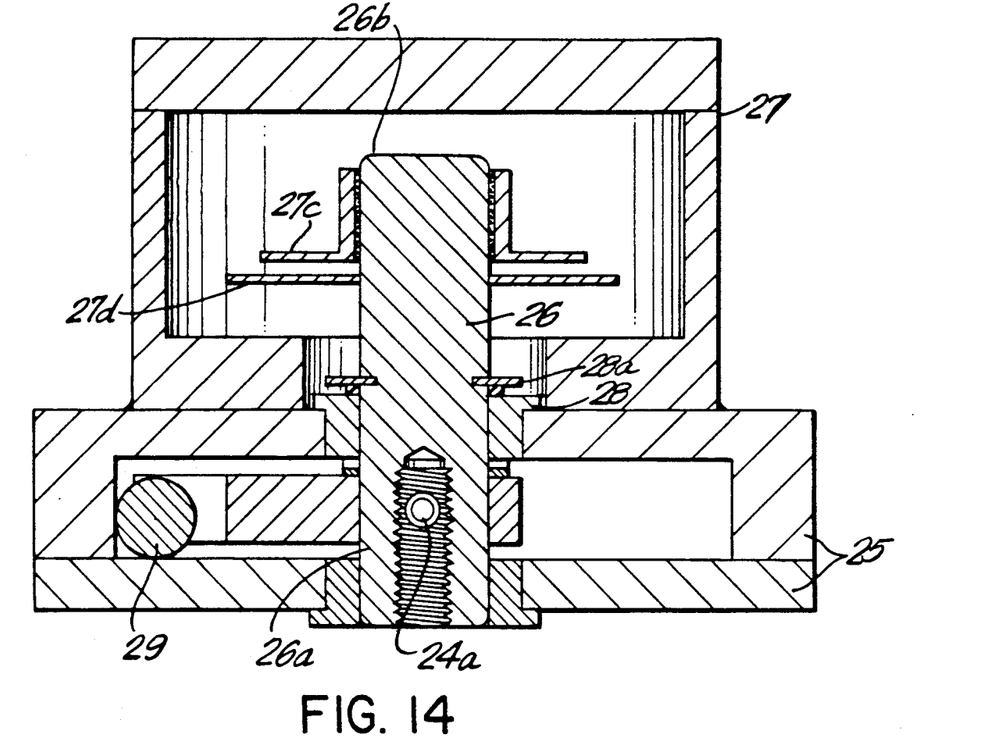
FIG. 14 is an enlarged cut-away section view along lines 14—14 of FIG. 13.
Figure 15:
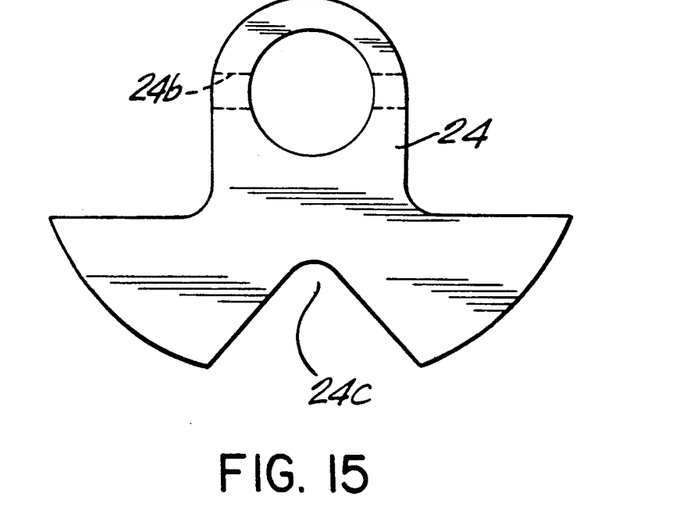
FIG. 15 is an elevational view in isolation of the pendulum contained within the interface unit.

Also shown in FIG. 14 is the stationary phase plate 27d of the encoder 27 which has apertures such that the light beam from the encoder 27 is transmitted only when the apertures in the code wheel 27c and the apertures in the phase plate 27d line up. In the present embodiment, during one complete revolution of the shaft 26, there will be 720 alternating light and dark periods. The optical information is then translated into generated electrical signals, in the form of electrical pulses, and transmitted to the microprocessor in the control unit 10 for processing.

Figures 10, 11:
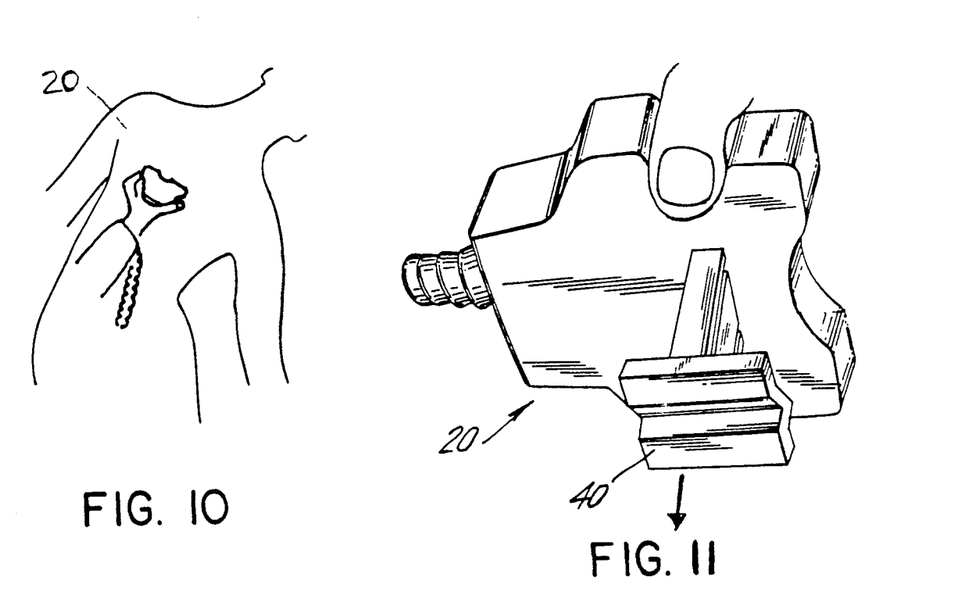
FIG. 10 is a front view showing the patient in a lateral bend position.
FIG. 11 is a perspective view of a lateral attachment for use with the interface unit when the patient engages in lateral bending as shown in FIG. 10, wherein the lateral attachment is placed against the side of the patient in the direction of the arrow.

The device of the present invention may also be used to determine angular position or angular range of motion in the lateral plane, for example, when a person bends side to side, as shown in FIG. 10. Lateral attachment 40, shown in FIG. 11, is adapted to be attached to the interface unit 20, for example, for snap-fitting into the interface unit 20, so that a lateral plane measurement can be made. The interface unit 20 with attached lateral attachment 40 is placed against the body segment or articulating joint in the direction of the arrow of FIG. 11.

Figure 12:
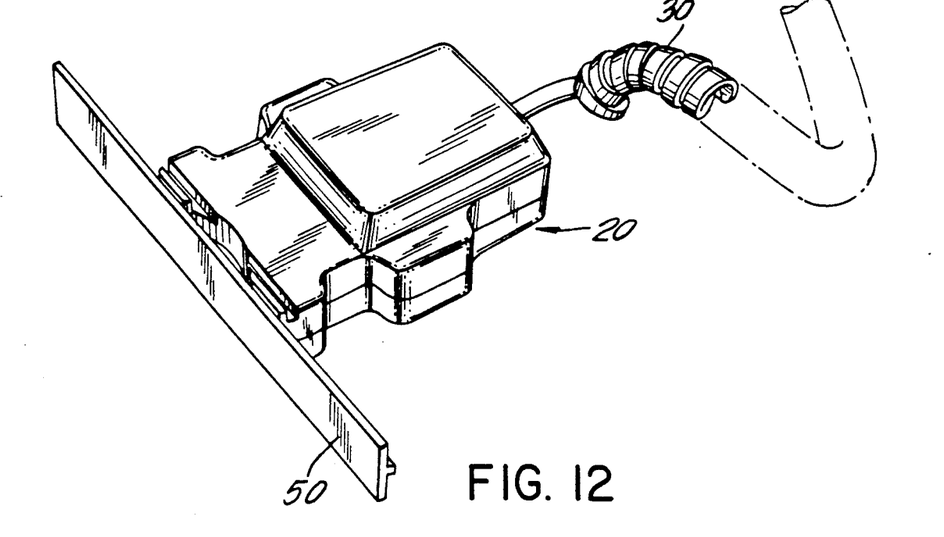
FIG. 12 is a perspective view of an x-ray attachment for use with the interface unit on an x-ray film.
Figure 13:
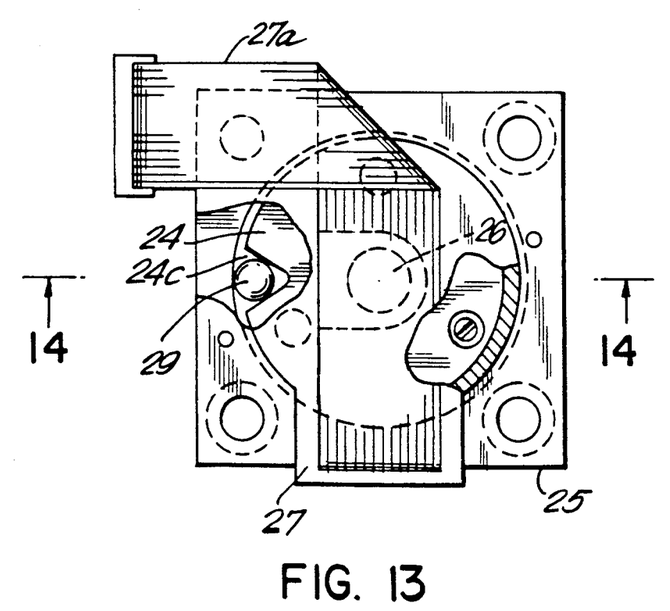
FIG. 13 is an elevated, partially cut-away view of a potion of the interface unit along lines 13—13 of FIG. 7, except that the pendulum of FIG. 7 is rotated 90° counterclockwise.
Figure 16:
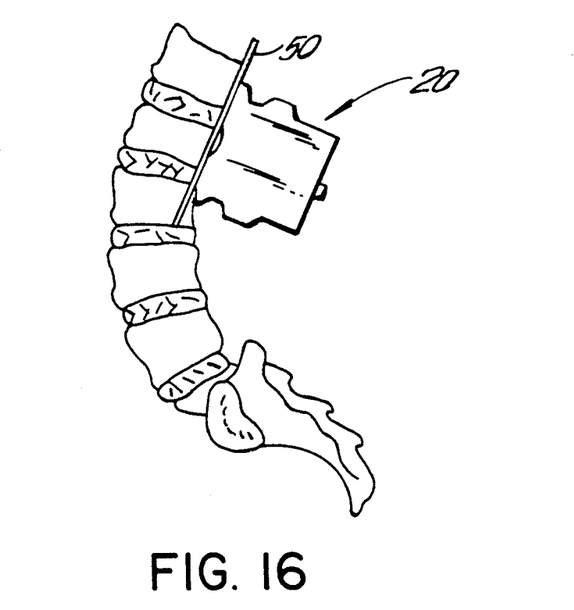
FIGS. 16-17 are each plan views of x-ray films, with the interface unit and the attached x-ray attachment of FIG. 12 placed on the film in each figure.
Figure 17:
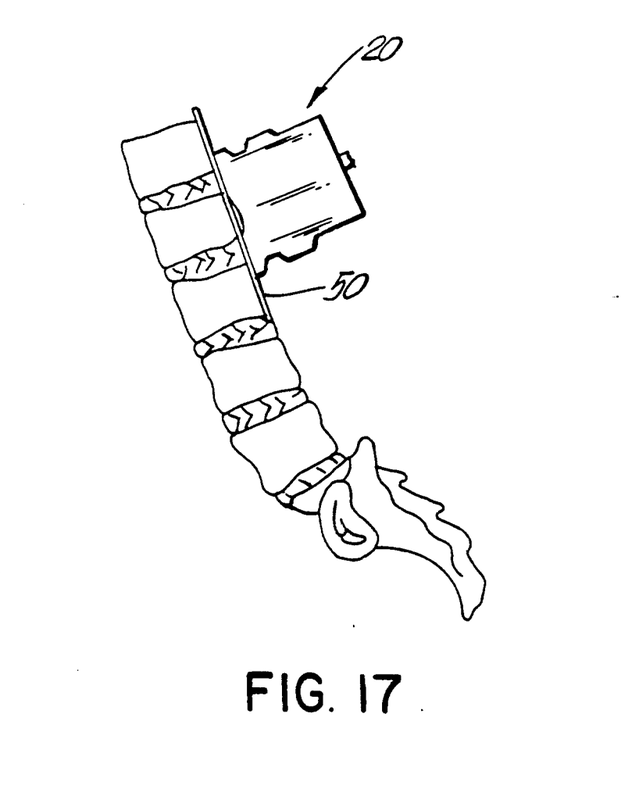

The device of the present invention, using the x-ray attachment 50 shown in FIGS. 12, 16 and 17, may be used to measure angular displacement on an x-ray film in several ways. As described below in the Protocol Section, the device with x-ray attachment 50 may be used to verify the results of external measurements such as those shown in FIGS. 8–9, and may also be used to measure subtle angular displacements such as interarticular changes, or to quantify the degree of deformity, such as in scoliosis.

Protocol Selection

Figure 19:
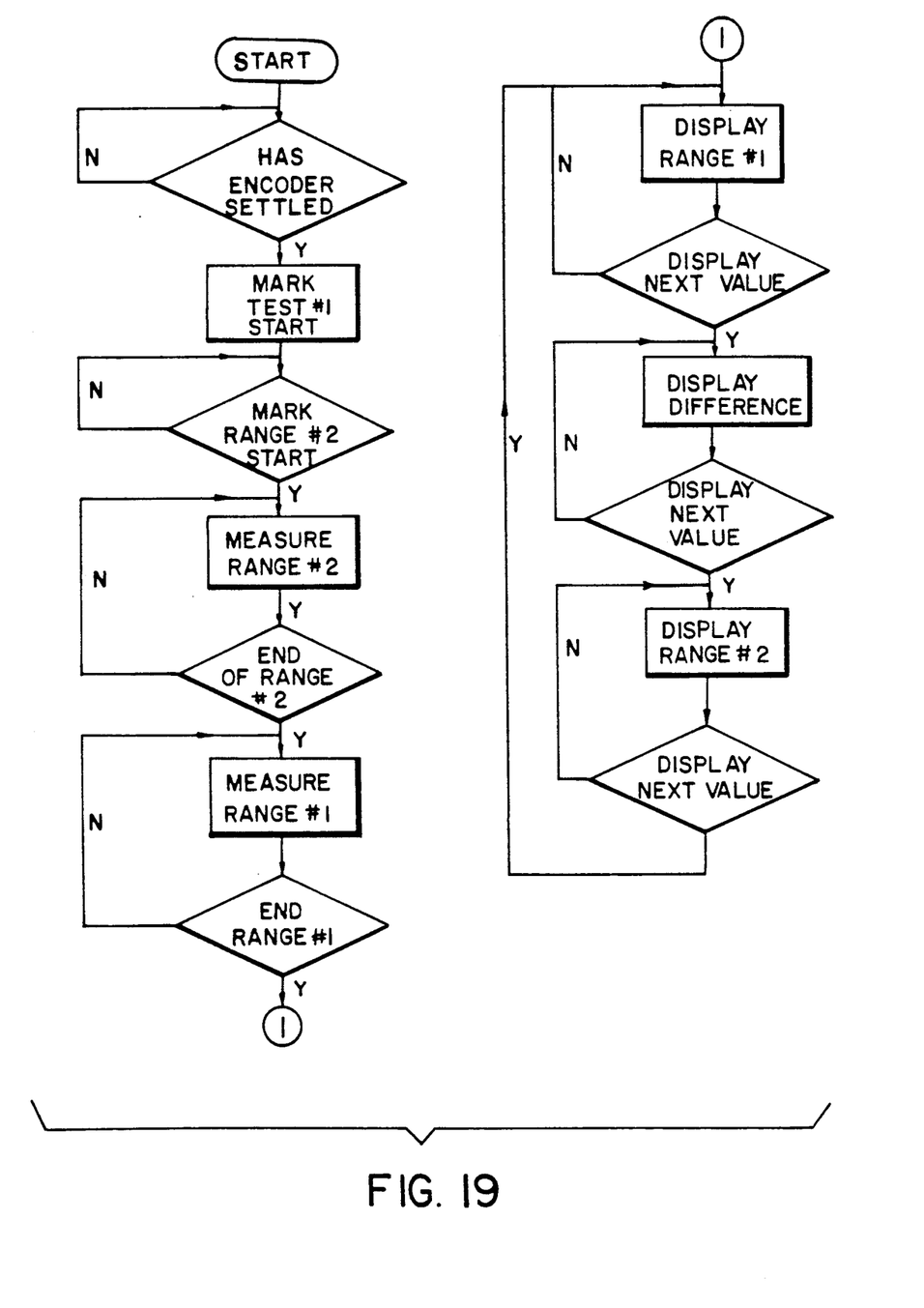
FIG. 19 is a flow chart showing the programmed steps for operating the device of the present invention in a compound-mode protocol.

The microprocessor in the control unit 10 may be programmed for any number of protocol operations. "Protocol" in the context of this invention means the calculations incorporated in the software by which the specific angular positional displacements are reported to the user. Below are described some protocol procedures which can be programmed in a conventional manner into the microprocessor of the control unit 10. FIG. 19 shows the steps for one such representative protocol in flow chart form, the so-called compound mode protocol. It is understood that any number of protocol operations are possible and may be programmed into the microprocessor.

Single Reference Mode Protocol

Figure 8:
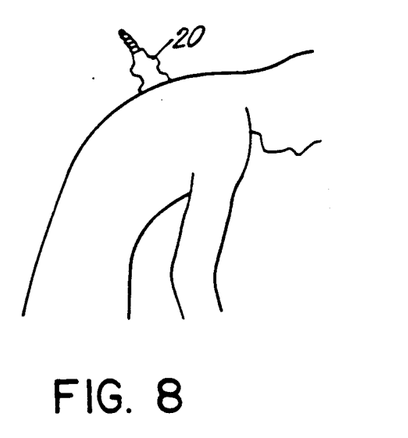
FIG. 8 is a side view showing the application of the interface unit to the spine while a patient is in the flexion position.
Figure 9:
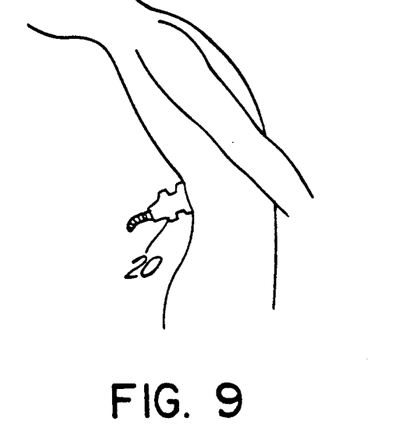
FIG. 9 is a side view showing the application of the interface unit to the spine while the patient is in the hyper-extension position.

This protocol, which is activated by depressing the Continuous switch 13, offers the ability to test total angular range of motion of one body segment or articulating joint at one location on the body segment or articulating joint while the patient is moved from a first anatomical angular position to a second anatomical position, for instance from the straight-up position to the flexion position (FIG. 8) or the hyper-extension position (FIG. 9).

The interface unit 20 is placed by the physician or clinician (hereafter "the operator") on the body segment or articulating joint to be tested. The patient is then positioned into the first anatomical angular position and set button 23 is depressed, providing a reference point. The set button 23 is electrically connected to the microprocessor in the control unit 10 and acts in most cases to provide reference points.

With the interface unit 20 stabilized by the operator against the body segment or articulating joint the patient is allowed to move. The control unit 10 will provide a continuous readout on the display 12 of angular displacement from the first angular position point during the movement.

At the end of the anatomical range of motion of the patient or at the point of pain, or at any other defined point in the angular motion, the set button 23 is again depressed and the last displayed relative angle will remain on the display 12. When the reset button 17 on the control unit 10 is depressed, the display 12 will clear and another test can begin.

The Single Reference Mode Protocol can also be used to measure the relative angle between two body segments or articulating joints at two locations for one anatomical position. To accomplish this, the operator places the interface unit 20 device in location on the first body segment or articulating joint to be tested. The patient is then positioned to the desired initial anatomical angular position. The operator depresses the set button 23, providing a reference point.

Making sure to keep the patient in the same anatomical position, the operator places the interface unit 20 on the second body segment or articulating joint to be tested. The operator depresses the set button 23. The last displayed angle will remain on the display 12. This will be the relative angle between the two locations chosen on the first and second body segments or articulating joints.

To verify the results of external measurements, i.e. measurements taken on the body segments such as those shown in FIGS. 8 and 9, the x-ray attachment 50 of FIG. 12 is used. The attachment 50 is adapted to be attached to the interface unit 20, for example, by securing the attachment 50 to the interface unit 20 by the tongue and groove method. As shown in FIG. 16, the device is placed flat on the x-ray film with the attachment 50 pressed against one edge of the image of the spine on the film. Set button 23 is depressed to provide a reference point. The device is then moved to another x-ray film showing the spine in a different angular position, such as that shown in FIG. 17, and the angular displacement from FIG. 16 to FIG. 17 is shown on the display 12. This allows the operator to verify the external angular displacement measurements previously made.

In order to measure interarticular changes, the displacement of specific segments (such as the lumbar vertebrae) can be measured by aligning the x-ray attachment 50 with the segments to be measured. A similar technique can be used to quantify degree of displacement in conditions such as scoliosis.

The function of the Continuous switch 13 is to measure angular displacement in a continuous fashion. Once the Continuous switch 13 is depressed, the unit will continue to collect displacement data regardless of ending position. This mode may be used for general assessment purposes. For example, the operator may instruct the patient to move through a range of motion and note where the patient feels some tightness or discomfort, but not restriction of motion. The operator can note the angle at which this tightness or discomfort occurs, and instruct the patient to continue moving until motion is restricted by pain or other physiologic factors. It is imperative, however, that the operator note the final angle of displacement, as the device will not lock in the value but will simply continue to collect data.

The Compound Mode Protocol

This protocol, which is activated by depressing the Compound switch 15, offers the ability to test total range of motion of two body segments (connected either directly or indirectly) from their own set reference points. For example, the operator can measure the combined range of the scapula and humerus which are directly connected via the glenoid fossa. One can also measure the total range of the hip and entire spine by using the sacrum and base of the occiput as reference points. These two anatomical landmarks are indirectly connected via the lumbar, thoracic, and cervical spine. The microprocessor in the control unit 10 will then calculate the differential range of motion between the two body segments. The primary goal of this protocol is to be able to obtain the relative range of motion between two body segments minus the effect of any other body position changes.

In this protocol, the angular range of motion of the second body segment selected should be related to the total angular range of motion of the first body segment selected; that is, the two body segments selected should be combined components of the total range of motion to be tested.

For example, trunk forward flexion is a combination of hip flexion and spine flexion. In order to assess the contribution of hip motion versus lumbar spine motion, the total motion of the hip and lumbar regions must be measured together, with total hip motion subtracted from total combined motion to calculate lumbar motion.

The operator places the interface unit 20 at the first location on the body segment to be tested. The operator then positions the patient at the anatomical starting position and depresses the set button 23, providing a first reference point.

Making sure to keep the patient in the same anatomical position, the operator places the interface unit 20 at a second location on the body segment to be tested. The operator then depresses the set button 23, providing a second reference point.

With the interface unit 20 at the second location on the body segment, the patient is allowed to move. The display 12 will provide a continuous readout of angular displacement from the second reference point during the movement.

At the end of the anatomical range of motion of the patient or at a point of pain, or at any other defined point in the angular motion, the set button 23 is depressed again and the last displayed angle will remain on the display 12. This angle is the total angular displacement of the body segment at the second location during the test.

Making sure to keep the patient in the same anatomical position, the operator places the interface unit 20 back at the first location on the body segment and depresses the set button 23. This will lock in the total range of motion for the first location of the body segment. The display 12 will now show the total angular displacement of the body segment at the first location during the test.

The interface unit 20 can now be removed from the patient. The operator depresses the set button 23 one more time and the microprocessor in the control unit 10 will calculate the differential angle between the first location and the second location on the body segment.

Since the control unit 10 is locked in a "display only" mode, the control unit 10 on the display 12 will redisplay the results previously shown in the following order each time the set button 23 is depressed:

total range of motion for the first location;
total range of motion for the second location; and
differential range of motion between the total range of motion for the first location and the total range of motion for the second location.

This will continue until the Reset button 17 is depressed.

Figure 18:
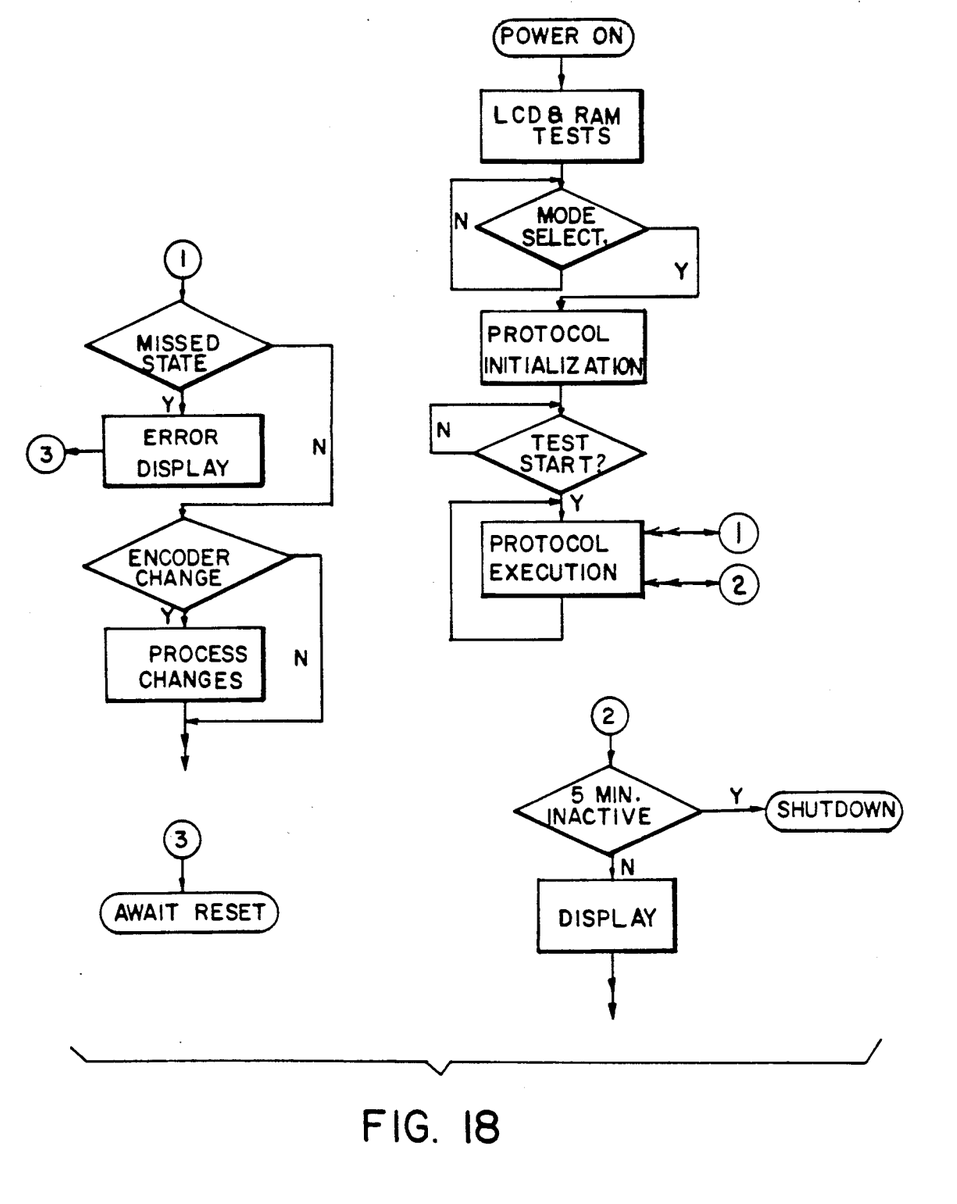
FIG. 18 is a flow chart of the overall operating scheme of the device of the present invention.

FIG. 18 is a software flow chart showing the basic system operation of the preferred embodiment of the device of the present invention. Referring to FIG. 18, after the operator turns on the device by depressing the On-Off switch 16 on the control unit 10, the system tests the liquid crystal display 12 and the random access memory in the microprocessor. The operator then selects an operating mode by depressing one of switches 13, 14 or 15. This step is represented by the block labelled "Mode Select" in FIG. 18. After the mode is chosen, the operator initializes the protocol by depressing the Reset switch 12 and, when the interface unit 20 is in the first or initial position on the body segment or joint, depressing the set button 23.

As the device is moved to a different angular position, the system registers a start of the test (the block labelled "Test Start" in FIG. 18) and executes the desired protocol. If the device is moved too quickly such that the microprocessor is unable to read all of the electrical pulses from the encoder 27 ("Missed State" on FIG. 18), an error is displayed on the display 12 and the device will not execute another test until the Reset switch 17 is depressed. If there is no missed state, and the encoder 27 is generating electrical pulses, the microprocessor processes the pulses from the encoder 27 ("Process Changes" in FIG. 17) and displays on the display 12 information regarding angular position.

If at any time the device is inactive for five minutes or more, the device is automatically shut off to conserve battery power.

An advantage of the present invention is that at a later time, for example, after the patient undergoes physical therapy or other treatment, the procedures described above relating to any of the specified protocols or any other programmed protocols can be repeated and further measurements taken. The operator can determine if the patient's angular motion capabilities have improved or deteriorated. This is possible because at the later time the interface unit 20 can be stabilized against the body segment or articulating joint in exactly the same fashion as the first measurement, permitting absolute repeatability of the measurement parameters.

It is readily seen that the device of the present invention provides an accurate and fast method for measuring relative angular positional displacement and angular range of motion for body segments and articulating joints of the human skeleton. The interface unit 20 is compact and easy to hold, and the display 10 provides all information required and can be programmed for any number of different testing procedures.

Applicants' invention is not limited to the embodiment of the device or the method described above. It is further understood that applicants, invention is as set forth in the following claims:

We claim:

1. A method for measuring relative angular positional displacement between two locations on a single body segment or articulating joint of a human skeleton comprising the steps of:

placing a front end of an interface unit of an electronic device against a first location on the body segment or articulating joint wherein the body segment or articulating joint is at a first anatomical postion and wherein the interface unit includes a shaft mounted within a housing of the interface unit, an optical encoder mounted on a first end of the shaft and a pendulum mounted on a second end of the shaft;

generating in the interface unit a first reference electrical signal representative of a first angular position of the body segment or articulating joint at the first location;

placing the front end of the interface unit against a second location on the body segment or articulating joint wherein the body segment or articulating joint remains at the first anatomical position;

generating in the interface unit a second reference electrical signal representative of a second angular position of the body segment or articulating joint at the second location;

moving the body segment or articulating joint to a second anatomical position resulting in a third angular position at the second location of the body segment or articulating joint, wherein the front end of the interface unit remains against the second location;

generating in the interface unit a third electrical signal representative of the angular displacement between the first angular position and the third angular position;

placing the front end of the interface unit against the first location on the body segment or articulating joint resulting in a fourth angular position at the first location, wherein the body segment or articulating joint remains at the second anatomical position;

generating in the interface unit a fourth electrical signal representative of the angular displacement between the first angular position and the fourth angular position; and calculating a difference between the third electrical signal and the fourth electrical signal thereby determining relative angular positional displacement between the first location and the second location on the body segment or articulating joint.

2. The method of claim 1 also comprising the step of displaying on a visual display associated with the electronic device a value representing the angular displacement between the second angular position and the third angular position.

3. The method of claim 1 also comprising the step of displaying on a visual display associated with the electronic device a value representing the angular displacement between the first angular position and the fourth angular position.

4. The method of claim 1 also comprising the step of displaying on a visual display associated with the electronic device a value representing the relative angular displacement between the first location and the second location on the body segment or articulating joint.

5. The method of claim 1 also comprising the step of measuring angular displacement in a continuous fashion as the body segment or articulating joint moves.

* * * * *